United States Patent
Kesling

(10) Patent No.: US 7,131,836 B1
(45) Date of Patent: *Nov. 7, 2006

(54) BRACKET WITH BILAYER BASE CONFIGURED TO PRODUCE A CONTROL VALUE

(75) Inventor: Andrew C. Kesling, LaPorte, IN (US)

(73) Assignee: TP Orthodontics, Inc., Westville, IN (US)

( * ) Notice: Subject to any disclaimer, the term of this patent is extended or adjusted under 35 U.S.C. 154(b) by 330 days.

This patent is subject to a terminal disclaimer.

(21) Appl. No.: 10/691,799

(22) Filed: Oct. 21, 2003

Related U.S. Application Data

(63) Continuation-in-part of application No. 10/285,742, filed on Nov. 1, 2002, now Pat. No. 6,746,242.

(51) Int. Cl.
*A61C 3/00* (2006.01)
(52) U.S. Cl. ......................................................... 433/9
(58) Field of Classification Search .................... 433/8, 433/9
See application file for complete search history.

(56) References Cited

U.S. PATENT DOCUMENTS

| | | | |
|---|---|---|---|
| 3,250,002 A | 5/1966 | Collito | |
| 3,629,187 A | 12/1971 | Waller | |
| 3,745,653 A | 7/1973 | Cohl | |
| 4,204,325 A | 5/1980 | Kaelble | |
| 4,948,367 A * | 8/1990 | Haas | 433/9 |
| 4,978,007 A | 12/1990 | Jacobs et al. | |
| 5,015,180 A * | 5/1991 | Randklev | 433/9 |
| 5,098,288 A | 3/1992 | Kesling | |
| 5,183,403 A | 2/1993 | Masuhara et al. | |
| 5,219,283 A * | 6/1993 | Farzin-Nia et al. | 433/9 |
| 5,263,859 A | 11/1993 | Kesling | |
| 5,267,855 A * | 12/1993 | Tuneberg | 433/9 |
| 5,295,824 A * | 3/1994 | Wong | 433/9 |
| 5,575,645 A * | 11/1996 | Jacobs et al. | 433/9 |
| 5,697,780 A | 12/1997 | Tuneberg et al. | |
| 5,810,584 A | 9/1998 | Wong | |
| 5,813,853 A * | 9/1998 | Kesling | 433/9 |
| 5,890,892 A * | 4/1999 | Lemchen | 433/9 |
| 6,071,118 A * | 6/2000 | Damon | 433/9 |
| 6,432,141 B1 | 8/2002 | Stocks et al. | |
| 6,685,468 B1 * | 2/2004 | Kesling | 433/9 |
| 6,746,242 B1 * | 6/2004 | Kesling | 433/9 |
| 6,834,761 B1 * | 12/2004 | Kesling | 206/63.5 |

* cited by examiner

*Primary Examiner*—Ralph A. Lewis
(74) *Attorney, Agent, or Firm*—Lloyd L. Zickert

(57) ABSTRACT

A bilayer base for attaching appliances selected from the group consisting of a component of a dental appliance, an orthodontic appliance, or an orthopedic appliance to a bony part of the human body wherein the appliance part to be attached to the bony part of the body may be made of metal, ceramic, or plastic. The base permits the appliance to be ready for mounting and includes a cured layer of polymer resin mounted on the appliance and an uncured layer of substantially the same polymer resin over the cured layer which when cured becomes integral with the cured layer in attaching the appliance to a bony part of the body.

4 Claims, 4 Drawing Sheets

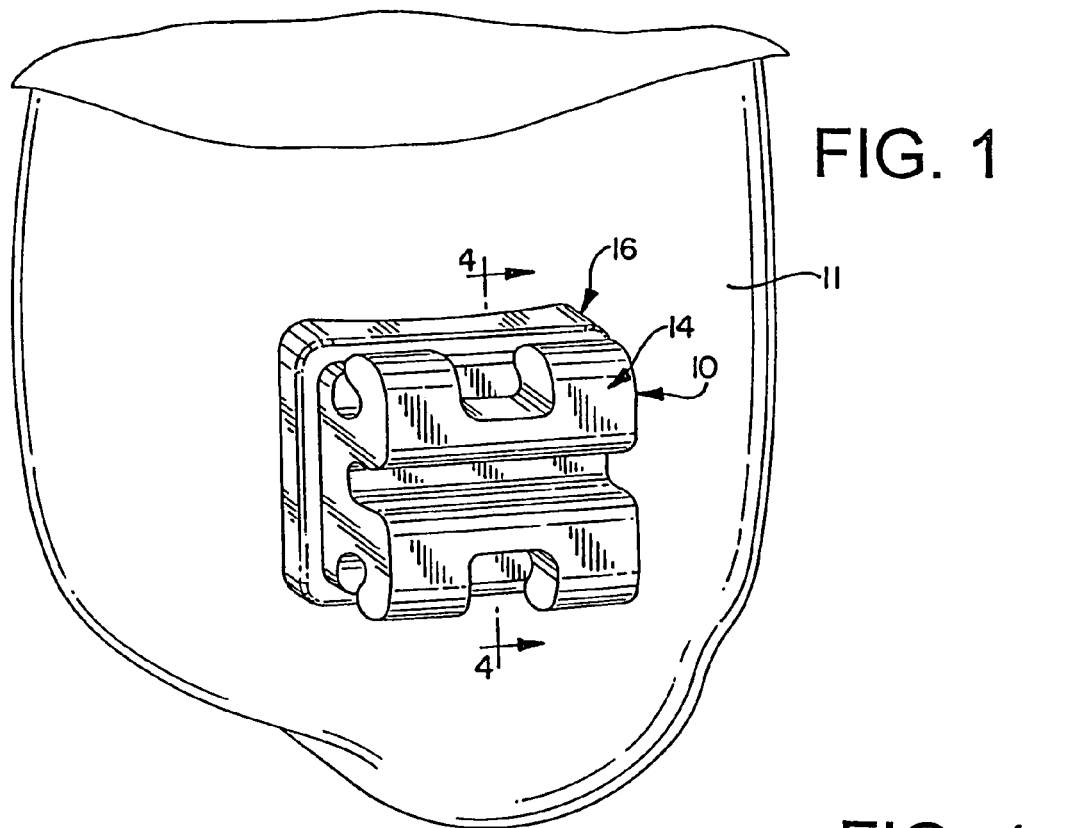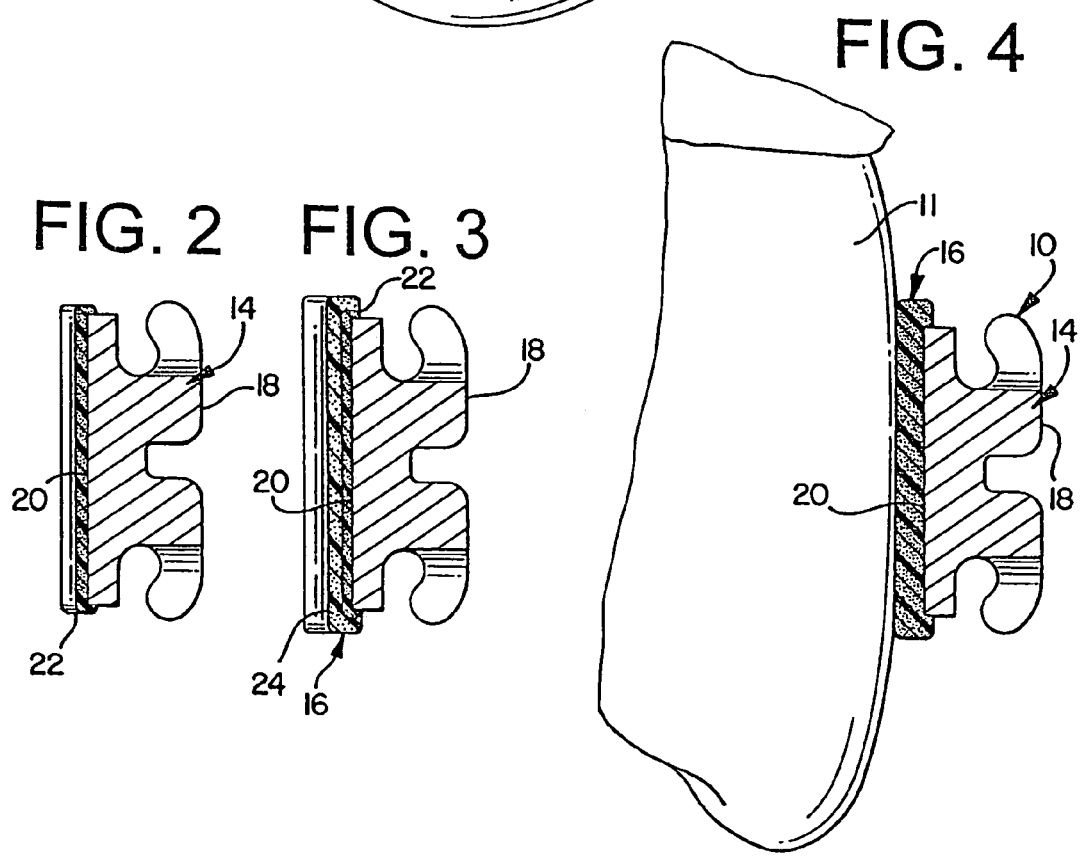

FIG. 5
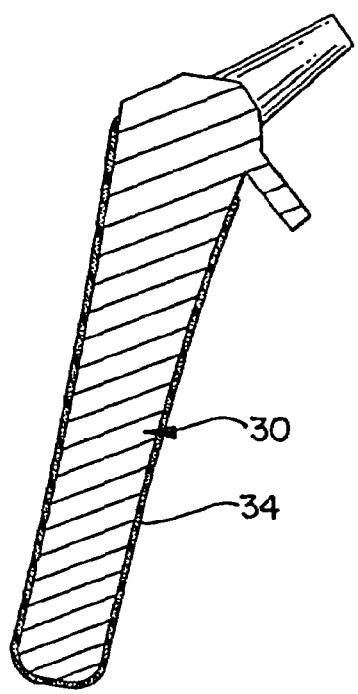
FIG. 6
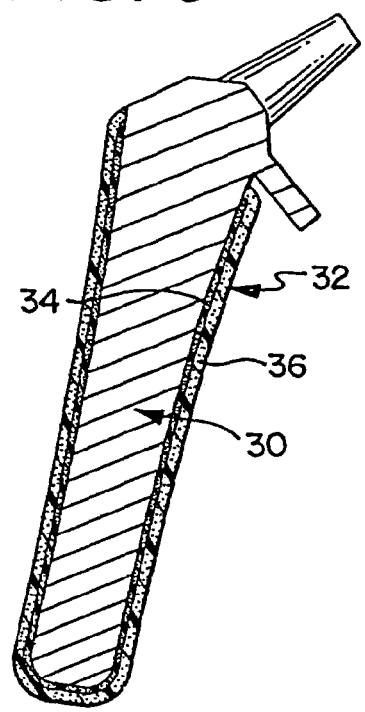
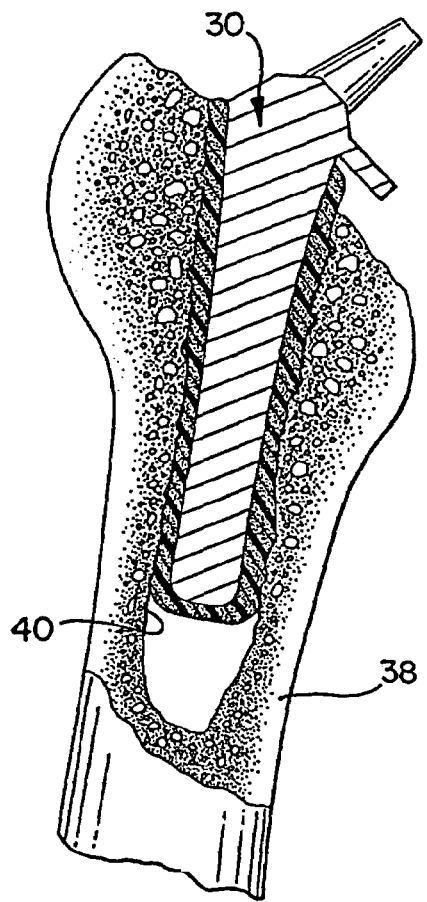
FIG. 7

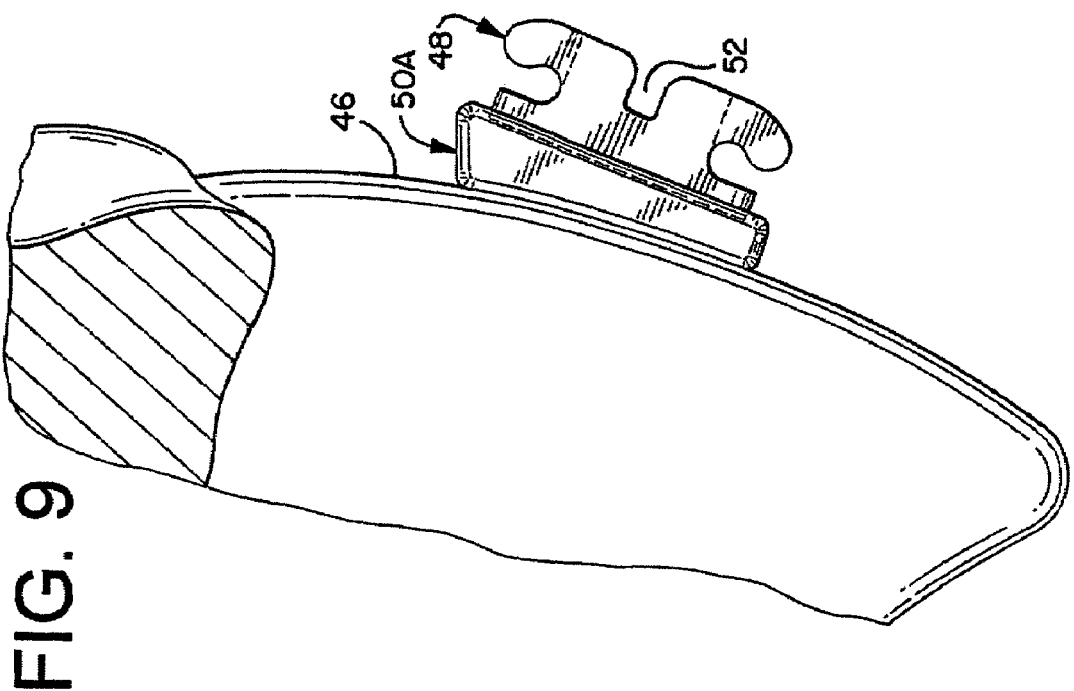
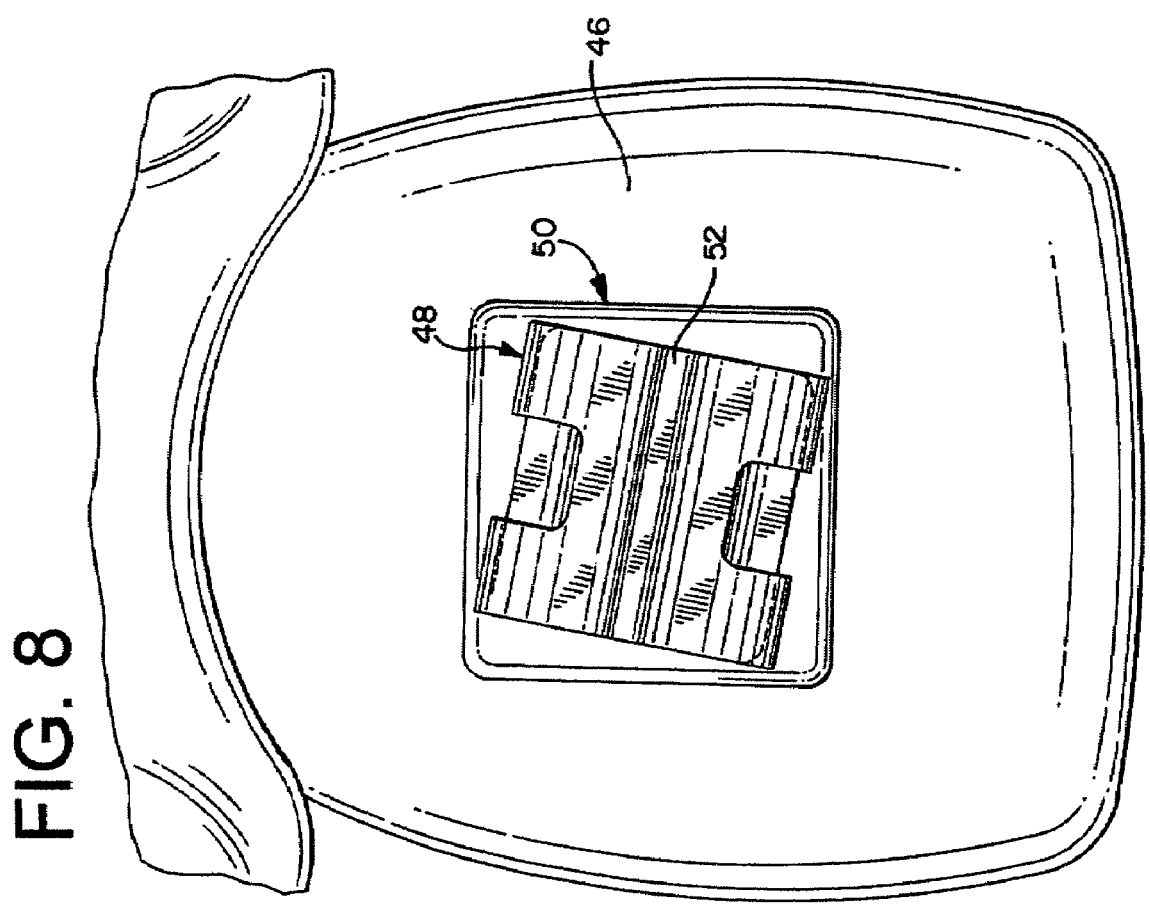

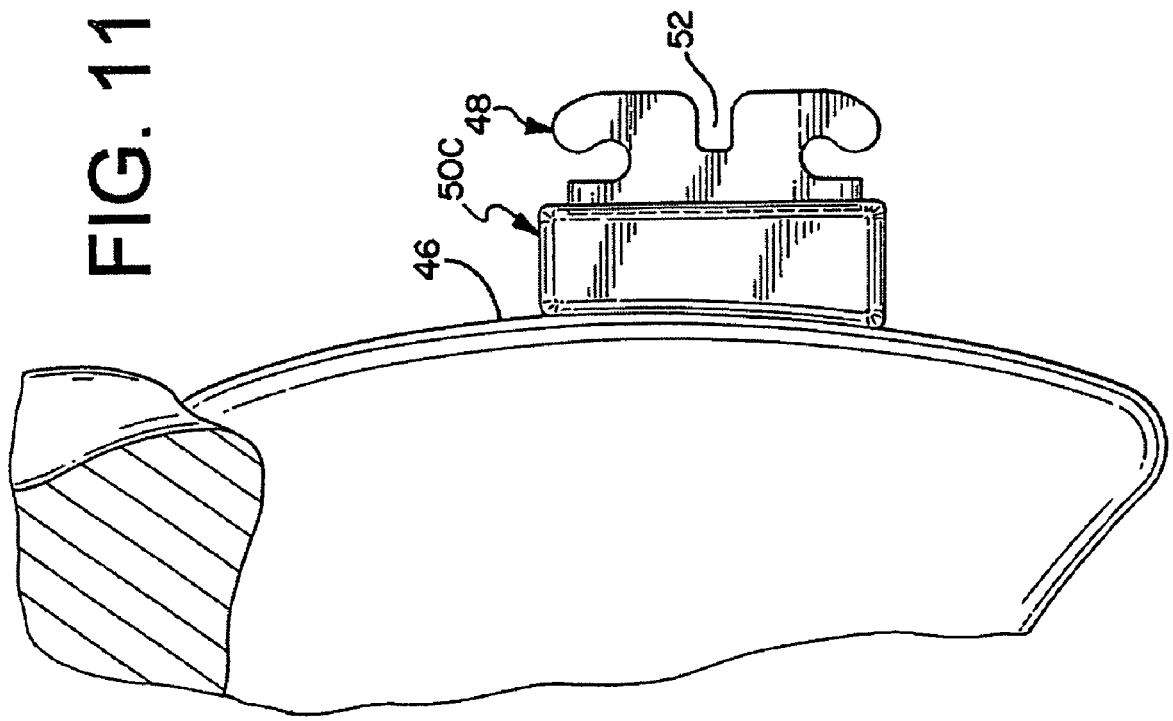
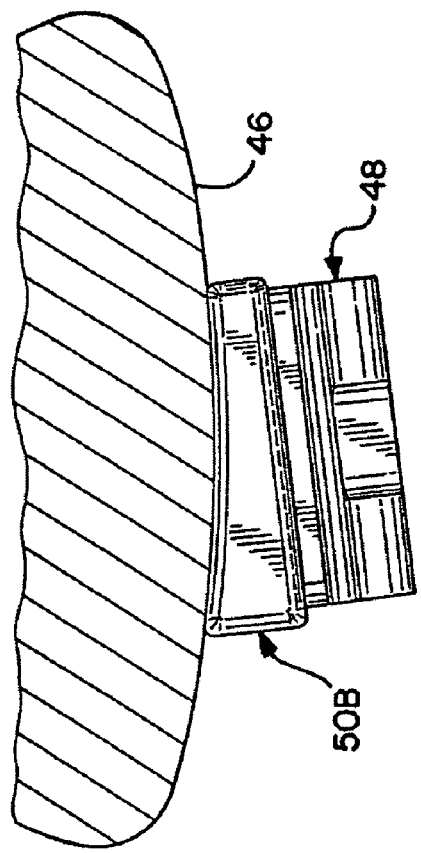

BRACKET WITH BILAYER BASE CONFIGURED TO PRODUCE A CONTROL VALUE

DESCRIPTION

This application is a continuation-in-part application of my application No. 10/285,742, filed Nov. 1, 2002, now U.S. Pat. No. 6,746,242.

This invention relates in general to a ready appliance for immediate attachment to a bony part of the human anatomy, and more particularly to an adhesive base on the appliance having a cured layer of plastic material attached to the appliance and an uncured layer of substantially the same material to be cured at the time of mounting the appliance and coacting with the bracket to produce a control value.

BACKGROUND OF THE INVENTION

Heretofore, it has been known to provide prepasted orthodontic appliances (appliances having uncured adhesive on the mounting side) to orthodontists for immediate mounting on teeth, without requiring the orthodontist to apply adhesive, like the appliances disclosed in U.S. Pat. Nos. 4,204,325 and 4,978,007. Such prepasted orthodontic appliances include a body provided with an uncured layer of chemically curable or light-curable adhesive on the mounting side which when cured attaches and secures the appliance to a tooth. It is well known that this type of an orthodontic appliance generally includes a metal mesh base to which the uncured layer of adhesive is applied prior to being sold to an orthodontist. And it is known that such an adhesive may be light-curable, chemically curable, or heat-curable, although light-curable adhesives like disclosed in the 4,978,007 patent are preferred.

An appliance with a cured polymer resin base has also been known for a ceramic orthodontic bracket, as disclosed in U.S. Pat. Nos. 5,098,288 and 5,263,859, wherein the base facilitates removal of the bracket from the tooth without damaging the tooth. Such brackets have been sold by TP Orthodontics, Inc. of LaPorte, Ind., under the trademark Mxi. The bases of these brackets have been transparent and translucent as disclosed in copending application Ser. No. 10/120,052 filed Apr. 10, 2002, now U.S. Pat. No. 6,786,720, and Ser. No. 10/224,770 filed Aug. 21, 2002, now U.S. Pat. No. 6,685,468, which applications are assigned to TP Orthodontics, Inc., like the present application, and are incorporated herein by reference.

SUMMARY OF THE INVENTION

The present invention is in providing a bilayer base for orthodontic appliances or orthopedic prosthetics to be ready for immediate mounting on the bony part of the human anatomy. The bilayer base includes a layer of cured plastic material of a suitable polymer resin and which is permanently mounted on the appliance. A further layer of uncured polymer resin is applied to the cured layer and the appliance is then suitably packaged and shipped to an orthodontic or orthopedic customer, who mounts the appliance onto a bony part of the human anatomy, cures the uncured layer of polymer resin, thereby defining an integral base that is cured onto the bony part of the human anatomy. With respect to the appliance constituting an orthodontic bracket prescribed for a chosen system for practicing the straight-wire technique, the bracket and/or the base may be configured to build in one or more functions or control values of tip, torque, rotation, and/or in/out compensation.

The polymer resin of the cured layer, as well as the uncured layer, is of substantially the same type and from the same family of resins and may be cured by light energy, chemical energy, or heat energy. Preferably the polymer resin is of a type that is light-curable, and with respect to this version, the cured layer serves to wick or transmit the curing light energy to the entire uncured layer, thereby enhancing the curing step to produce a strong bond. The cured layer of resin is of any suitable polymer resin such as an acrylic, an epoxy or an acrylic-based epoxy. For example, an orthodontic appliance, such as a bracket, that may be of metal, ceramic, or plastic would first be provided with a layer of the polymer resin which would be cured to define the first layer of a bilayer base. Secondly, an uncured layer of substantially the same polymer resin would be applied to the cured layer and the appliance with this bilayer base would be suitably packaged and shipped to an orthodontic customer, who would mount the bracket on a tooth, after suitably preparing the tooth, and thereafter cure or polymerize the uncured layer of resin to effect attachment of the bracket to a tooth.

As above mentioned, where the base of the invention is applied to an orthodontic bracket for a desired prescription or system for the well known straight-wire technique, a control value is preferably built in certain designated brackets, such as those mountable on certain anterior teeth, and more particularly the centrals, laterals, cuspids and bicuspids. Depending on the control value desired, the cured layer of the base will be sized and shaped or oriented relative to the bracket to produce the control value. It should also be appreciated that the front and/or side profile of the bracket may also be rhomboidally configured instead of the base to produce torque and/or angulation control values.

Similarly, the bilayer base can be used for orthopedic prosthesis assemblies such as where a hip, knee or other joint replacement is satisfied with the implantation of an orthopedic prosthesis. One part of the prosthesis would normally include a stem that would be inserted into a canal of a bone. According to the present invention, the stem would have the bilayer base of a suitable polymer resin and at the time of mounting on a bone the uncured layer of adhesive would be activated by light, chemical, or heat energy to attach the part to a bone of the human anatomy. As above explained with respect to the bilayer base on an orthodontic appliance having a light-cure resin, the cured layer serves as a light bar or conduit to allow the light energy to blanket the uncured layer.

Accordingly, the ready-made bilayer base of the present invention could be used in the dental or orthopedic field for attaching appliances to the bony structure of the body.

It is therefore an object of the present invention to provide a new and improved bilayer base for appliances to be mounted on bony parts of the body including teeth and bones.

Another object of the present invention is to provide for an appliance with a bilayer base to be mounted on a bony part of the body wherein because of the materials of the base a greatly enhanced bonding structure will be established between the appliance and the bony part of the body.

A further object of the present invention is to provide a ready appliance for the convenience of the user such as an orthodontic bracket having a bilayer base with a cured layer and an uncured layer of polymer resin that not only enhances the bonding strength of the base to a bony part of the body but also facilitates the removal of the base at a time when the bracket is to be removed.

A still further object of the present invention is to provide an orthodontic appliance, in the form of a bracket, tube or button with a ready bilayer base that facilitates the handling of the appliance at a time when used by an orthodontist to mount on a tooth wherein the bilayer base includes a cured layer of polymer resin on the appliance body and an uncured layer of polymer resin over the cured layer and from the same family of resins as the cured layer, wherein the uncured layer would be cured at the time of mounting the appliance on a tooth and form an integral base for the appliance.

A further object of the present invention is to provide a bilayer base including a transparent or translucent cured layer and an uncured layer of transparent or translucent light-curable resin for an orthodontic or orthopedic appliance, wherein the cured layer functions to wick or transmit the curing light energy over the entire layer of uncured resin to produce curing of the entire uncured layer and a better bond between the appliance and the surfaces on which the appliance is to be attached.

A still further object of the present invention is to provide a bilayer base for an orthodontic bracket having cured and uncured layers of polymer resin, wherein the cured layer of the base is configured and/or oriented relative to the bracket to produce a control value for the bracket.

Other objects, features and advantages of the invention will be apparent from the following detailed disclosure, taken in conjunction with the accompanying sheets of drawings, wherein like reference numerals refer to like parts.

DESCRIPTION OF THE DRAWINGS

FIG. 1 is a perspective view of an orthodontic bracket mounted on a tooth with the bilayer base of the present invention;

FIG. 2 is a vertical cross-sectional view taken through an orthodontic bracket like that in FIG. 1 wherein the first layer of the bilayer base has been applied to the bracket body and cured;

FIG. 3 is a view similar to FIG. 2 but also showing the layer of uncured polymer resin in place over the cured layer to define a bracket ready for mounting on a tooth;

FIG. 4 is a vertical sectional view taken substantially along line 4—4 of FIG. 1 and illustrating the second layer of the base cured and that it becomes integral with the initially cured layer to provide the complete base for the appliance according to the present invention;

FIG. 5 is a cross-sectional view of an orthopedic prosthesis having the initial cured layer of the bilayer base according tot the present invention;

FIG. 6 is a view similar to FIG. 5 and further showing the layer of uncured polymer resin over the cured layer of polymer resin and thereby depicting the appliance as it would be delivered to a user desiring to install the appliance on the bone of a person;

FIG. 7 is a sectional view taken through the appliance of FIGS. 5 and 6 and a bone to which the appliance is attached and illustrating the cured and uncured layer as being integral and attached to the bone of a person;

FIG. 8 is a front or buccolabial elevational view of a bracket having the base of the invention configured so that the bracket includes a tip or angulation control value;

FIG. 9 is a labiolingual view of a bracket having the base of the invention wherein the base of the bracket is configured with a torque control value;

FIG. 10 is a top plan view of a bracket having a base of the invention where the base is configured to give the bracket a rotation control value; and FIG. 11 is a side elevational view of a bracket having the base of the invention configured to provide the bracket with a prescribed in/out control value.

DESCRIPTION OF THE INVENTION

Referring now to the drawings, and particularly to FIGS. 1 to 4, an orthodontic bracket 1 is shown in mounted position on a tooth 11 in FIGS. 1 and 4 to illustrate the invention. It will be appreciated that the bracket 10 includes a bracket body 14 and a base 16.

While the bracket body 14 illustrates a bracket of a type that is sold by TP Orthodontics, Inc. of LaPorte, Ind., it will be appreciated with respect to the invention the bracket body may be of any suitable type and of any suitable material. Moreover, the invention, being directed primarily to the base, can be used on any appliance that would be mounted on a tooth, including a bracket, a molar tube, or a lingual button, an implantable stem for a tooth implant, or other appliance desired to be bonded to a tooth or the jaw for purposes of dentally or orthodontically treating a patient. Thus, the appliance body 14 may be of any type that would be useful in treating the dentition of a patient, orthodontically or otherwise, where it would be desired to adhesively bond an appliance in a desired place. Moreover, as will be discussed further below, the base of the invention can be used for orthopedic appliances to mount a part of a prosthesis on a bone of a person.

The body of the appliance, and in this case the bracket 14, may be made of any suitable material for an orthodontic appliance, such as metal like stainless steel, ceramic, or plastic. Similarly, if the appliance body is a buccal tube, it can be made of any of these materials. As seen particularly in FIGS. 2, 3 and 4, the bracket body 14 includes an archwire receiving side 18 and a base receiving side 20. The base 16 is mounted onto the base receiving side 20.

The bracket is made by suitably preparing the surface of the bracket body and then molding or otherwise applying a first layer 22 of a polymer resin to the bracket and then curing that layer. Preferably, the layer includes edges that overlap the edges of the bracket body as illustrated in order to provide the best possible bonding or connection between the layer 22 and the bracket body and also enhance the transmission of light during the curing of the second layer. This step of the manufacture is illustrated in FIG. 2 where only the cured layer 22 is shown on the mounting side of the bracket.

Next, a second layer 24 of a polymer resin is suitably applied over the first layer 22. This layer is maintained in an uncured state, and therefore the appliance is provided to the orthodontic customer so that the orthodontist, after preparing the tooth on which the bracket is to be mounted, can merely apply the bracket with the bilayer base onto the tooth and then cure the second layer 24 accomplishing the mounting or attachment of the bracket to the tooth. Once the second layer is cured, it will merge and be essentially integral with the first layer as the base of the bracket, as shown in FIG. 4, and thereby provide the complete bonding connection between the bracket and the surface of the tooth 11.

The polymer resin of the first layer 20 may be acrylic, epoxy or acrylic-based epoxy resin, or any other suitable resin. Further, the resin may be of a type that is light-curable, chemically curable, or heat-curable. Preferably, the resin is of a type that is light-curable. Moreover, the second layer 24 is of a polymer resin in the same polymer resin family as the polymer resin of the first layer 22. Preferably, the polymer resins are substantially identical to one another, and an acrylic-based epoxy that is light-curable. As long as the resins of each layer are from the same family, which enhances the bonding between the layers, the curing/polymerization process of each need not be the same. For example, the cured layer may be heat cured, while the uncured layer may be light-curable.

Referring now to the embodiments of FIGS. 8 to 11, the bilayer base of the invention is configured and/or oriented such as to produce a control value in the bracket and base such as to produce tip or angulation, torque, rotation, or in/out compensation. A tip control value produces a tipping movement of a tooth that may be defined as a pivotal movement at the long axis of a tooth in a mesiodistal direction. A torque control value produces a torque movement that may be defined as the pivotal movement of the long axis of a tooth in a buccolingual direction. A rotation control value produces a rotational movement of the tooth about its long axis, and in/out compensation value produces a predetermined spacing between the bracket and the tooth face on which it is mounted for the archwire. While brackets with specified control values may be used in any orthodontic technique, they are particularly useful for practicing the straight-wire technique. Moreover, the control values may be provided for any bracket on any tooth but primarily control values are used for the centrals, laterals, cuspids and bicuspids.

Depending upon the prescription of a chosen system, one or more control values may be built into any one bracket. However, it will be appreciated that for most systems the control values are particularly applicable for brackets mountable on centrals, laterals, cuspids and bicuspids. Although one or more control values may be built into any one bracket, for purposes of explaining how the control values may be built into a bracket, each of FIGS. 8, 9, 10 and 11 illustrates individually the control values above identified. In each of the FIGS. 8 to 11, a bracket is mounted on the labiobuccal face of a tooth.

An illustration of the manner of producing a tip or angulation control value in a bracket having the bilayer base of the present invention is shown in FIG. 8 wherein the bracket 48 is oriented onto the base 50 such that horizontally open archwire slot 52 extends angularly of the base 50. When bonding the bracket and base on the tooth, the vertical axis of the base 50 is aligned with the long axis of the tooth 46, while the bracket 48 is angularly related to the base, thereby placing the archwire slot at an angle to the long axis of the tooth. Depending on whether the desired tip angle is positive or negative will determine whether the slot is to be positioned as illustrated on the base or tilted to the opposite position. In the position illustrated, the archwire slot would extend downwardly and to the right, while in the opposite position the archwire slot would extend downwardly and to the left. Accordingly, a tip control value is incorporated in the base and bracket of FIG. 8 by inclining the bracket to the base. It will be appreciated that any suitable bracket style having an open rectangular archwire slot like the slot 52 in the bracket 48 may be used.

With respect to building a tip or angulation control value into a bracket, or any of the hereafter described control values, it will be appreciated that the bracket may be of a suitable metal or metal alloy, ceramic, or plastic material. After suitably preparing the surface of the bracket body receiving the base the first layer of polymer resin of a suitable thickness is molded to the body of a thickness suitable for the required function of the bracket, and then suitably cured thereby attaching the layer to the bracket body. Thus, the first layer is mounted onto the base as above mentioned.

It may also be appreciated that the tip control value may be built into the bracket and base by rhomboidally configuring the labiobuccal profile of the bracket as has been well known.

Referring now to FIG. 9, the same bracket 48 is shown for illustrating the building in of a torque control value into the bracket and base. The base in this view is identified as 50A and is mounted on the face of the tooth such that the vertical axis of the bonding base coincides with the vertical or long axis of the tooth like the base 50 in the embodiment of FIG. 8. However, the thickness of the cured layer of the base 58 is greater at one end, and in this case the gingival end, in order to cause tilting of the bracket 48 and downwardly directing the archwire slot which produces a torque control value. Again, the torque control value may be positive or negative depending upon the system used. In this embodiment, it can be seen that the buccolingual axis of the archwire slot 52 extends downwardly to the right in order to produce the desired torque control movement. While the manner of producing the control value or function of torque is accomplished by the configuration of the base 50A, it could be accomplished by rhomboidally configuring the buccolingual profile of the bracket as is well known.

The embodiment of FIG. 10 differs from the embodiments of FIGS. 8 and 9 in that the bracket and base are configured such that the base 50B is configured to produce a rotation value for causing rotation of the tooth 46 in a desired direction. Accordingly, the base 50B is wedge-shaped differently from the wedge-shaped base 50A so as to space one of the mesial or distal ends of the bracket further away from the base of the tooth 46. It will be appreciated that the configuration of the base may be such as to provide a positive or negative rotation control value by adjusting the thickness of the mesial or distal end of the cured layer of the base.

The embodiment of FIG. 11 illustrates a bracket and base combination which produces an in/out compensation control value. As illustrated, it will be noted that the base is deeper in order to position the bracket 48 further outwardly from the face of the tooth. Similarly, the in/out compensation could be such as to reduce the spacing of the bracket from the face of the tooth, and this control value produces a spacing between the face of the tooth and the archwire held in the archwire slot 52.

It should be appreciated that any one bracket and base combination could have built in more than one control value. For example, a bracket and base combination could be configured such that both tip and torque control values are built into the bracket and base.

It will be appreciated that the bracket with the bilayer base having a cured layer of polymer resin and an uncured layer of polymer resin will be shipped and transported to a customer in such a way as to protect the integrity of the uncured layer and also prevent it from curing during the time it is in transport. One method of transporting the appliance with the bilayer base is to flush it with nitrogen to preserve the uncured state of the adhesive resin and then hermetically seal it in a package to prevent light from activating the curing cycle of the uncured adhesive. Where the base is of a light-curable resin, the transparent or translucent cured layer further functions as a light conduit for the curing light energy to allow the energy to fully activate the uncured layer of resin and fully cure the layer to fully bond the appliance to the mounting surface. Thus, the light energy wicks or moves easily along the cured layer. One of the layers may be transparent, while the other layer is translucent. Preferably, the cured layer is transparent to optimize the transmission of the curing light energy.

Thus, the bracket of the invention, having a bilayer base, is ready for the orthodontist to mount on a tooth and thereafter to direct a curing light at the uncured layer of the polymer resin to cure the layer and firmly attach the bracket to a tooth.

The bilayer base of the invention is illustrated as being applicable to an orthopedic prosthesis in FIGS. 5 to 7, wherein FIG. 6 shows an elongated stem 30 over which the bilayer base 32 has been formed to define a prosthetic part ready to be used by the orthopedic customer for attachment to a bone following light-curing of the uncured layer of the base. The base 32 includes a cured layer 34 of a polymer resin over which an uncured layer 36 of substantially the same, if not the same, polymer resin is provided to complete the base.

FIG. 5 shows the orthopedic stem 30 with only the cured layer 34 applied to the stem in the manufacture of the bilayer base. Thereafter, the uncured layer 36 is added before shipping the stem to an orthopedic customer, as shown in FIG. 6.

It will be appreciated that the orthopedic prosthesis stem 30 could be made of any suitable material, such as metal, ceramic, or plastic, and be formed for use in any articulated part of the human anatomy. The particular appliance stem 30 shown is intended to be used for a hip replacement procedure to replace a part of a diseased femur 38. A canal 40 is suitably formed, such as by drilling, in the end of the femur and into which the end of the prosthetic device is inserted.

It will be appreciated that with respect to artificial knee replacements, as well as hip replacements, cemented and uncemented prostheses may be used. The present invention relates only to the use of a cemented prosthesis, and as above mentioned, the stem 30 may be made of any suitable material although it is usually made of metal. Again, the appliance with the bilayer base as shown in FIG. 6, wherein the outer layer 36 is provided in an uncured state before being provided to a customer like the above described orthodontic appliance. Also, like an orthodontic appliance with the base of the invention, the prosthesis would be flushed with nitrogen and then hermetically sealed in a container that would not allow any light transmission to prevent curing of the light-curable polymer resin layer of the bilayer base when shipping the prosthesis to an orthopedic customer.

It will be appreciated that the polymer materials of the bilayer base may be of the same type as above identified with respect to the orthodontic appliance. And where the polymer material of the uncured layer is light-curable, and the cured layer is transparent or translucent, the cured layer further functions to wick or transmit the light energy of a curing light to the entire uncured layer.

FIG. 7 illustrates the orthopedic part 30 having its bilayer base in place in a canal of a femur and the uncured layer, wherein the cured and uncured layers of the base integrally join together during the time the uncured layer attaches to the bone of the femur and connects the part to the femur.

It will be appreciated that the illustrations of an orthodontic bracket and a part of a prosthetic artificial joint are merely illustrative of the scope and use of the bilayer base according to the invention as it could be used in connection with any artificial part that is to be secured to a bone or tooth of the body.

It will be understood that modifications and variations may be effected without departing from the scope of the novel concepts of the present invention, but it is understood that this application is to be limited only by the scope of the appended claims.

The invention claimed is:

1. The combination of an orthodontic bracket and a laminated base for ready mounting of the bracket on a tooth, wherein the bracket includes an outwardly opening mesiodistally extending archwire slot and said base and/or its orientation with the bracket opening includes a built-in control value, said base comprising:
    a first layer of cured polymer resin of uneven thickness mesiodistally and integral with the bracket, and
    a second layer of uncured polymer resin of substantially the same family as the first layer defining a tacky surface for ready mounting of the bracket on a tooth, and
    said bracket and/or said cured first polymer resin layer of said base being configured to coact with the archwire slot to at least produce a rotation control value.

2. The combination of an orthodontic bracket and a laminated base for ready mounting of the bracket on a tooth, wherein the bracket includes an outwardly opening mesiodistally extending archwire slot and said base and/or its orientation with the bracket opening includes a built-in control value, said base comprising:
    a first layer of cured polymer resin of uneven thickness occlusogingivally and integral with the bracket, and
    a second layer of uncured polymer resin of substantially the same family as the first layer defining a tacky surface for ready mounting of the bracket on a tooth, and
    said bracket and/or said cured first polymer resin layer of said base being configured to coact with the archwire slot to at least produce a torque control value.

3. The combination of an orthodontic bracket and a laminated base for ready mounting of the bracket on a tooth, wherein the bracket includes an outwardly opening mesiodistally extending archwire slot and said base and/or its orientation with the bracket opening includes a built-in control value, said base comprising:
    a first layer of cured polymer resin integral with the bracket, and
    a second layer of uncured polymer resin of substantially the same family as the first layer defining a tacky surface for ready mounting of the bracket on a tooth, and
    said bracket and/or said cured first polymer resin layer of said base being configured to coact with the archwire slot to at least produce a tip value wherein said cured first polymer resin layer is oriented on the bracket in non-alignment therewith to produce said tip control value.

4. The combination of an orthodontic bracket and a laminated base for ready mounting of the bracket on a tooth, wherein the bracket includes an outwardly opening mesiodistally extending archwire slot and said base and/or its orientation with the bracket opening includes a built-in control value, said base comprising:
    a first layer of cured polymer resin integral with the bracket, and
    a second layer of uncured polymer resin of substantially the same family as the first layer defining a tacky surface for ready mounting of the bracket on a tooth, and
    said bracket and/or said cured first polymer resin layer of said base being configured to coact with the archwire slot to at least produce an in/out compensation value wherein the value is the result of the labial-lingual thickness of said cured first polymer resin layer.

* * * * *